US010311535B2

(12) United States Patent
Corral et al.

(10) Patent No.: US 10,311,535 B2
(45) Date of Patent: Jun. 4, 2019

(54) TEXT-MESSAGING BASED COACHING PROGRAMS

(71) Applicant: CareMessage, San Francisco, CA (US)

(72) Inventors: Cecilia Guadalupe Corral, Pharr, TX (US); Manuel Antonio Rivera de la Vega, San Francisco, CA (US)

(73) Assignee: CareMessage, San Francisco, CA (US)

( * ) Notice: Subject to any disclaimer, the term of this patent is extended or adjusted under 35 U.S.C. 154(b) by 0 days.

(21) Appl. No.: 14/537,612

(22) Filed: Nov. 10, 2014

(65) Prior Publication Data

US 2015/0269697 A1 Sep. 24, 2015

Related U.S. Application Data

(63) Continuation-in-part of application No. 14/220,901, filed on Mar. 20, 2014, now abandoned.

(51) Int. Cl.
*G06Q 50/22* (2018.01)
*H04W 4/12* (2009.01)

(52) U.S. Cl.
CPC .............. *G06Q 50/22* (2013.01); *H04W 4/12* (2013.01)

(58) Field of Classification Search
CPC ................................ G06Q 50/22; H04W 4/12
See application file for complete search history.

(56) References Cited

U.S. PATENT DOCUMENTS 8,321,242 B1 * 11/2012 Morton et al. ................ 705/3

OTHER PUBLICATIONS

Stephanie Bauer, Judith de Niet, Reinier Timman, and Hans Kordy. Enhancement of care through self-monitoring and tailored feedback via text messaging and their use in the treatment of childhood overweight. Patient Education and Counseling, vol. 79, Issue 3, Jun. 2010, pp. 315-319.*
Co-Pending U.S. Appl. No. 14/220,901 of Rivera de la Vega, M.A., et al., filed Mar. 20, 2014.

* cited by examiner

*Primary Examiner* — Linh Giang Le
(74) *Attorney, Agent, or Firm* — Perkins Coie LLP

(57) ABSTRACT

Technology is directed to an interactive text message based coaching program ("the technology"). A user enrolled in a campaign interacts with a server to obtain guidance on performing a set of tasks of the campaign to achieve a health goal. The user interacts with the server via text messages using a mobile computing device. After the health goal of the user is identified, the server generates text messages having information related to the campaign. The text messages are generated based on the health goal for the user, and are customized for the user. The server sends the text messages to the user in a sequence, wherein a next text message of the sequence sent to the user is based on a response received from the user for a previous text message of the sequence.

28 Claims, 12 Drawing Sheets

TEXT-MESSAGING BASED COACHING PROGRAMS

CROSS-REFERENCE TO RELATED APPLICATION(S)

This application is a continuation-in-part of U.S. patent application Ser. No. 14/220,901, entitled "TEXT-MESSAGING BASED COACHING PROGRAMS" filed on Mar. 20, 2014, which is incorporated by reference herein in its entirety.

TECHNICAL FIELD

At least one embodiment of the technique introduced here relates to text messaging campaigns, and more particularly, to interactive text messaging campaigns.

BACKGROUND

A campaign program is a plan to achieve an objective, usually over an extended period of time. The campaign program usually coordinates many activities and uses of resources involving multiple organizations. A campaign program can also have subordinate objectives or intermediate milestones and is often broken down by phases. Campaign programs are often created for health care services, financial services, and other areas. A health campaign program, for example, can be conducted for offering guidance on various health related topics such as weight loss, a workout routine, etc. A finance campaign program can be conducted, for example, to offer guidance on finance related topics such as investments, saving a percentage of monthly income, etc. Traditional campaign programs are typically conducted using media such as email, telephone, print media and television.

Current campaign programs are typically targeted to a general audience, even though they may be intended for only a specific group of people who may be interested in a particular campaign. Further, the campaign programs are typically not customized to specific individuals. Consequently, such campaigns are not very effective because they fail to target the right group of individuals and because they are not relevant to every individual. For example, a health campaign program for weight loss which suggests a general weight loss diet may be relevant to an individual who generally prefers Mexican Cuisine, but may not be relevant to another individual who prefers Italian Cuisine.

Some email based campaign programs are targeted to a set of participants. However, email is not an effective medium for conducting campaign programs. Some studies suggest that only 28% of emails are reportedly read within a few minutes of receipt, and therefore fail to prompt the participants to respond. Accordingly, the current campaign programs are not effective.

DETAILED DESCRIPTION

Figure 1:
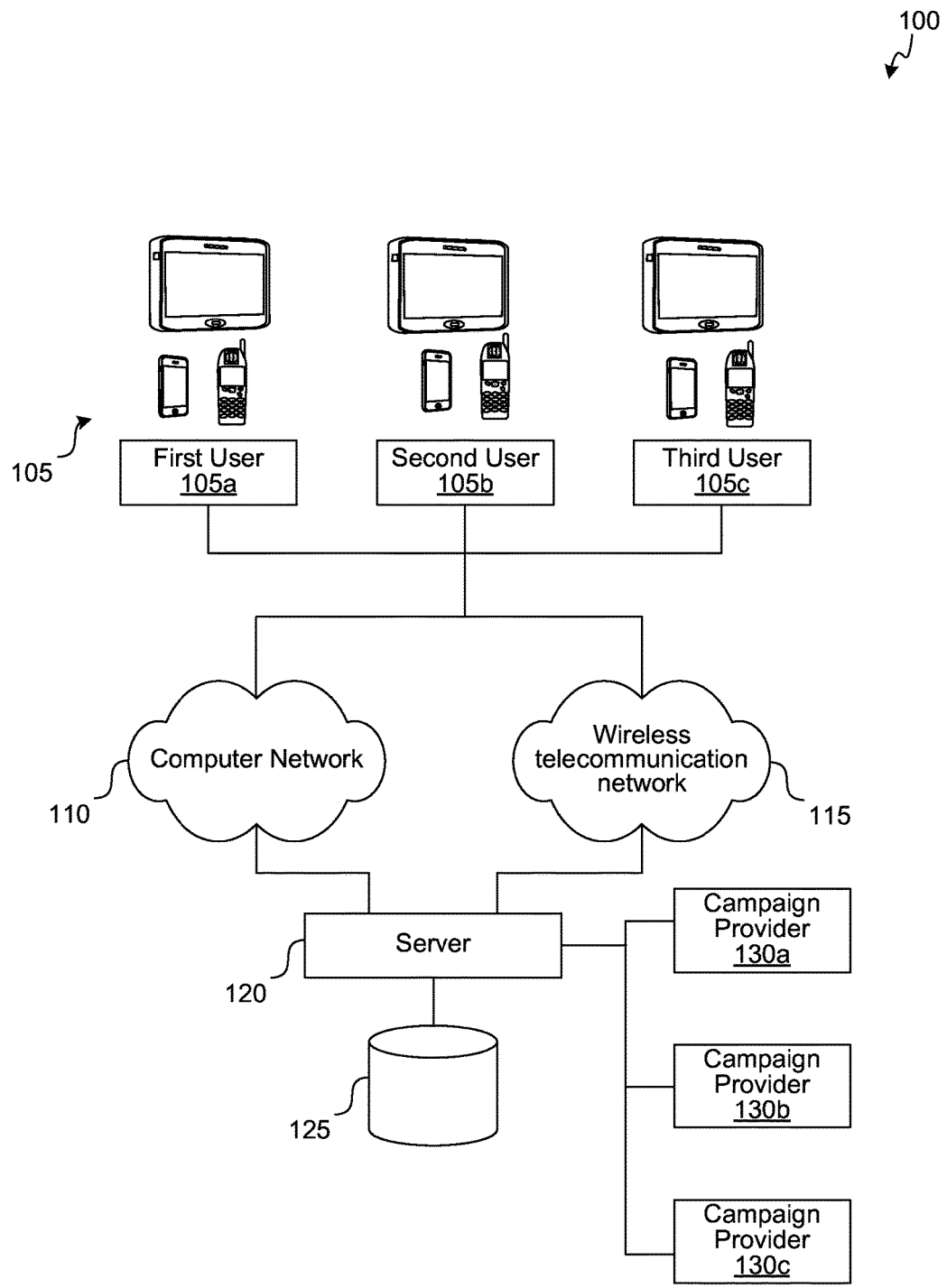
FIG. 1 is a block diagram illustrating an environment in which the text message campaign program can be implemented.

In this description, references to "an embodiment", "one embodiment" or the like, mean that the particular feature, function, structure or characteristic being described is included in at least one embodiment of the technique introduced here. Occurrences of such phrases in this specification do not necessarily all refer to the same embodiment. On the other hand, the embodiments described are not necessarily mutually exclusive.

Introduced here is technology for a text message based interactive campaign program ("the technology"). In one embodiment, a user interacts with a server to obtain guidance on performing a set of tasks of the campaign to achieve a specific goal. For example, the user enrolled in a health campaign can obtain information on performing a set of tasks to achieve a particular health goal such as lowering blood sugar level. The user can interact with the server via short text messages using a mobile computing device, for example, by using short messaging service (SMS) with a smartphone. After the user identifies the health goal, the server automatically generates the text messages having information related to the campaign. The text messages are generated based on the health goal for the user, and are customized for the user. The campaign program is designed as an interactive program where text messages are generated such that at least some of the text messages prompt the user to respond. The server sends the text messages to the user in a sequence. The sequence also can be customized to the user. That is, the next text message in the sequence sent to the user is based on a response received from the user for a prior text message in the sequence.

In some embodiments, the sequence of the text messages sent to the user is determined by using a decision tree, which logically connects the text messages of the campaign with other text messages by use of a tree (data) structure. In the decision tree, a particular interactive text message is connected to one or more other text messages that follow the particular text message. Only one of the text messages is identified as the next message to be sent based on one or more criteria. In some embodiments, if the particular message is a message that requires a response from the user, the next message is determined depending upon the most recent response received from the user. In this manner, the text messages sent to the user are customized for the user. For example, in a health campaign program for managing diabetes, text messages sent to a diabetic individual can be customized based on the blood sugar level of the individual at a particular day and time. The campaign program can send a text message asking the user to provide a reading of the individual's blood sugar. The campaign program can send a text message suggesting a next step based on the blood sugar level received from the user. For example, if the blood sugar level received from the individual is in a first range, then the campaign program can send a text message reminding the individual to take an insulin shot. If the blood sugar level is in a second range, then the campaign program can send a text message acknowledging the individual and asking the individual to continue to control the dietary habits.

In some embodiments, the text messages can also be multimedia messages and can be sent to the mobile computing device of the user using messaging services provided by the wireless telecommunications network such as multimedia messaging service (MMS) or the like. The text messages can also be sent via a computer network such as Internet, for example, by using a social networking application.

The technology also includes a campaign creation tool that enables a user, such as a campaign provider or a campaign manager, to create the text messages for a particular campaign. In some embodiments, the campaign creation tool is a graphical user interface (GUI) tool. The campaign creation tool includes an interaction component that can be used by the user to create various types of text messages for the campaign. For example, an information-only type interaction component can be used to generate a text message that provides information to the user and does not expect a response from the user. A response type interaction can be used to generate a text message that prompts a response from the user. An open ended type interaction can be used to generate a text message for which (i) the user may or may not reply and (ii) the response from the user is expected in no particular format. The user can create an instance of the interaction component and input the information into the instance that has to be sent as a text message to the user. Various such instances can be created and each of the instances can be linked to one or more of the instances (e.g., using the GUI) defining the sequence in which the corresponding text messages are sent.

Environment

FIG. 1 is a block diagram illustrating an environment 100 in which the text message based campaign program can be implemented. The environment 100 includes a server 120 that provides a text messaging infrastructure for sending text messages related to a campaign program to a set of users, such as a first user 105a, a second user 105b and a third user 105c, participating in the campaign program. The server 120 sends the text messages to a mobile device associated with the users 105a-c. The campaign program can be a set of tasks to be performed by a user, e.g., first user 105a, to achieve a particular goal. For example, a campaign program can be a health program, such as a weight loss program, and a goal can be a health goal such as "lose 20 pounds in a month." In another example, the health program can be a program for managing diabetes, and a goal can be to bring down the blood sugar level to a certain value within a month. In yet another example, a campaign program can be a finance program, such as a program on saving a percentage of monthly income, and the goal can be "saving 10% of salary."

Continuing with the health program example, the text messages sent by the server 120 to the first user 105a can include informational text messages such as the diet to be followed, exercises to be done, etc. The text messages can also include question-answer type text messages that require the first user 105a to respond to the text messages. For example, the question-answer type text message sent to the first user 105a can be "Did you exercise today? Yes/No." The first user 105a may respond to the question by sending a text message containing "Yes" or "No" as the answer.

The interactive process of exchanging the text messages between the first user 105a and the server 120 can continue for the period of the campaign program or until the first user 105a identifies that he has achieved the goal, for example. In some embodiments, the text messages are sent to the corresponding mobile devices of the users 105a-c using a text messaging service provided by the wireless telecommunication network 115 of their corresponding mobile devices, via a wireless telecommunications network. In some embodiments, the text messages are sent to the corresponding mobile devices of the users 105a-c using another type of computer network 110, such as Internet. For example, the text messages can be sent to the users 105a-c over the computer network 110 via social networking applications, such as Twitter, Instagram, WhatsApp etc. The users 105a-c can access the social networking applications on their mobile devices to view and/or reply to the text message. In some embodiments, the text messages can be sent as emails and/or as voice messages.

The text messages sent to the users 105a-c are customized for each of the users 105a-c. In some embodiments, before sending the campaign program text messages, the server requests the users 105a-c to identify their goals, such as exercising, saving a percentage of their paycheck for the month, etc. The server requests the users to set their (1) overall goal, (2) frequency of the goal, or individual sub-goals, (3) scope of the goal, such as the amount of money to spend or save, or the number of minutes to walk, etc. (4) reason for achieving the goal, (5) confidence level in meeting the particular goal etc. Based on the responses, the server 120 will automatically create text messages customized for each of the users 105a-c. In some embodiments, the server 120 creates text messages customized for a group of users who the campaign program considers similar. For example, two users having approximately the same weight and same eating habits and want to lose the same amount of weight in a given period may be considered to be similar. In another example, two users who want to save the same percentage of their paycheck may be considered to be similar. A campaign provider who creates the campaign program can define the criteria for determining similar users.

The text messages are sent to the users in a particular sequence. A next text message of the sequence sent to the user is determined based on a response received from the user for a previous text message of the sequence. For example, if a text message is a question asking the user, "How many calories did you burn? (A) 50-100, (B) 101-150, (C) 151-200," the next text message to be sent to the user depends on the response provided by the user. Accordingly, the text messages sent to the users are tailored for the user rather than being generic. Further, the users 105a-c can specify their preferences for receiving the text messages. For example, the users 105a-c can specify the schedule—day, date, time, frequency, an occurrence of an event, etc. for receiving the text messages.

The server 120 can support campaign programs in various sectors, including healthcare, education, financial services, politics, etc. A number of campaign providers such as a first campaign provider 130a, a second campaign provider 130b and third campaign provider 130c can use the server 120 to provide their campaign programs to the users 105a-c. In some embodiments, the server 120 is managed by an entity different from that of the campaign providers 130a-c. The campaign providers 130a-c can create their campaign programs and provide them to the server 120. The server 120 generates the text messages of the corresponding campaign programs and sends them to the users 105a-c. Further, the entity managing the server 120 can also create campaign programs. In some embodiments, the server 120 enables a campaign program created by one entity be shared with other entities. For example, a finance campaign program created by a second campaign provider 130b can be shared with a third campaign provider 130c who provides a real estate campaign program. This enables the campaign providers to target a broader set of users and/or a relevant group of users.

The server 120 also analyzes various aspects of the campaign programs and generates statistical data. Some examples of statistical data can include a response rate (RR), which is a percentage of texts asking for an answer that have been replied; a response speed (RS), which is a time between question sent and answered received; a response speed in 5 min (RS-5MIN), which is a percentage of texts asking for an answer replied within 5 minutes of reception; a response speed in 12 hours (RS-12H), which is a percentage of texts asking for an answer replied within 12 hours of reception; and a drop-off rate (DR), which is a percentage of opt-outs replies in the total number of replies received. In some embodiments, the campaign providers can track how their campaign programs are performing and/or modify certain aspects of the campaign program to enhance the performance of the campaign programs based on the statistical data.

A storage facility 125 is used to store various data for the operation of the server, including user profile data of users 105a-c, campaign programs provided by one or more of campaign providers 130a-c, profile data of campaign providers 130a-c, statistical data, etc. In some embodiments, the storage facility 125 is or includes a database.

Figure 2:
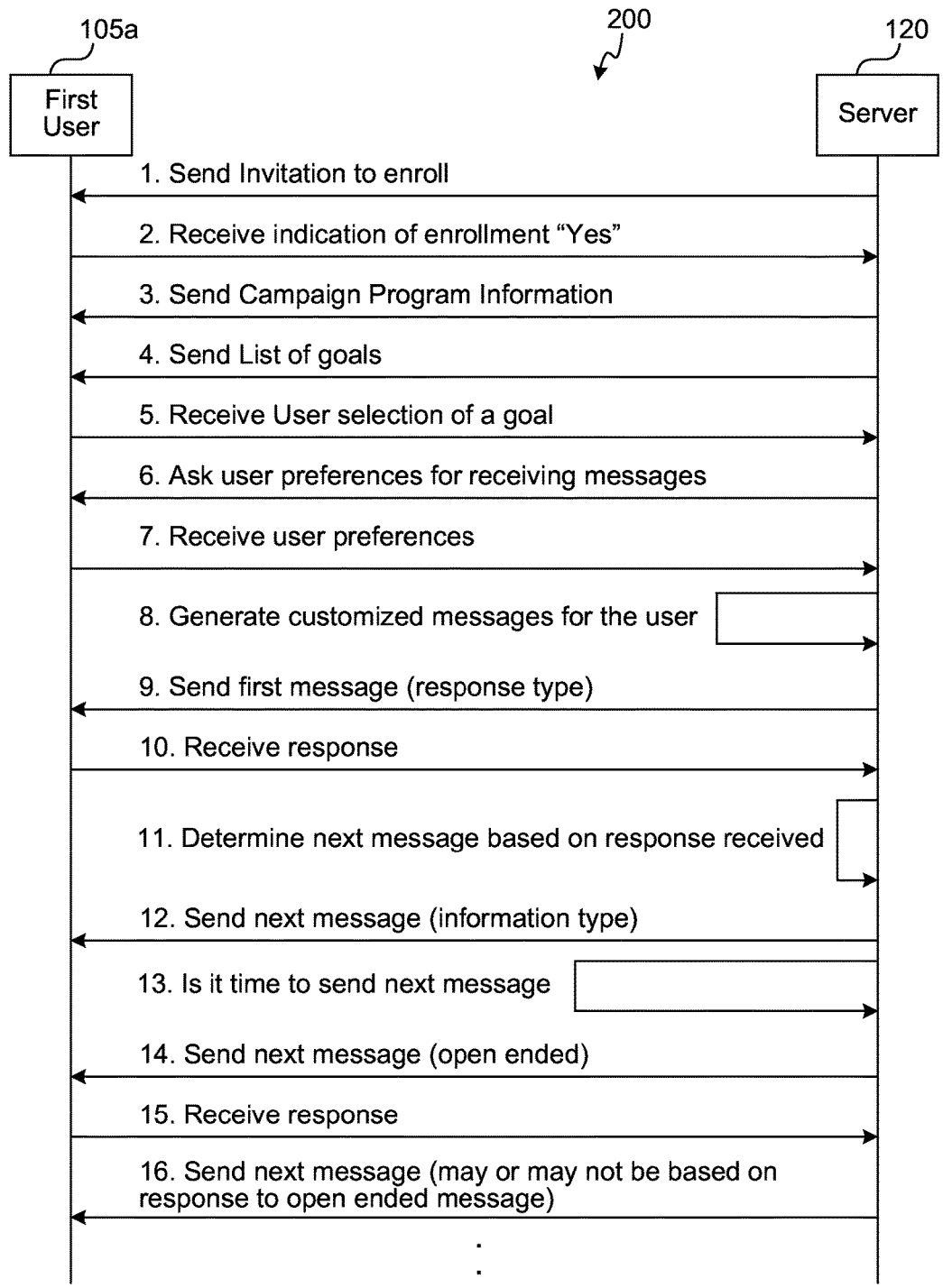
FIG. 2 is a sequence diagram illustrating an example of an interaction between a user and a server facilitating a campaign program.

FIG. 2 is a sequence diagram 200 illustrating an example of an interaction between a user and a server facilitating a campaign program. The interaction illustrated in the sequence diagram 200 can occur in the environment 100 of FIG. 1. Further, consider that the campaign program on which the first user 105a is interacting with the server 120 is a health coaching program for weight loss. In some embodiments, each of the text messages sent to the user has a unique purpose, including imparting knowledge, encouraging a behavior, or to obtain a piece of data by the first user 105a. The text messages sent to the first user 105a is based on the unique circumstances and preferences of the first user 105a. In some embodiments, the text messages mirror the experience of a live health coaching session. The text messages sent to the first user 105a by the server 120 are sent by the server 120 automatically.

At step 1, the server 120 sends a text message to the mobile computing device of the first user 105a inviting the first user 105a to enroll for the health coaching program. The text message can also include other information such as the provider of the health coaching program, etc. At step 2, the first user 105a responds by sending a text message indicating that the first user 105a is interested in enrolling for the health campaign. The first user 105a user may indicate his interest in the response text message in various ways, for example, by including "Yes" in the text message. In another example, first user 105a can be asked to select one of the choices provided in the text message of interaction 1 to indicate his interest. If the first user 105a indicates that he is not interested, the server 120 may acknowledge the decision of the first user 105a and stop sending any messages further.

After the first user 105a enrolls, at interaction 3, the server 120 can send a text message having additional information about the health coaching program. The text message of step 3 can be an information type interaction, which does not require the first user 105a to respond.

At step 4, the server 120 sends a list of health goals to the first user 105a. For example, the list of health goals can be "(A) Lose 5 pounds in a week, (B) Lose 20 pounds in a month, (C) Low Carb Diet, or (D) Other." At step 5, the first user 105a can respond by sending a text message having one of the choices.

At step 6, the server 120 sends a text message asking the user to identify the user preferences. The user preferences can include, for example, a language in which the first user 105a likes to receive the text messages in, a schedule according to which the first user 105a likes to the receive the text messages, etc. At step 7, the first user 105a responds by sending a text message specifying the user preferences.

At step 8, the server 120 generates, but does not necessarily immediately send, the text messages related to the health coaching program for the first user 105a, based on the health goal selected by the user and/or other user preferences. The manner of generating the text messages is described below in greater detail.

At step 9, the server 120 sends the first text message of the health coaching program to the first user 105a. For example, the text message can be a question asking the first user 105a to identify his dietary preferences. At step 10, the first user 105a responds by sending a text message specifying his (e.g., dietary) preferences. Since the campaign program is customized for the user, knowing the preferences of the first user 105a helps to choose subsequent messages to advise the first user 105a, for example, to manage the diet. Accordingly, at step 11, the server 120 determines the next text message to be sent to the first user 105a based on the preferences specified in the response received from the first user 105a. At step 12, the server sends the next text message to the first user 105a. For example, a Spanish-speaking diabetic user can identify his or her eating habits to align more closely with Mexican cuisine. This will allow the server 120 to, at step 12, send the first user 105a low-carb recipes related to some of the staple foods within that demographic, where, for instance, tomato, onion and garlic are the base for many soups and sauces. On the other hand, if the first user 105a identifies his eating habits as Italian cuisine, other recipes may be sent at step 12.

In another example, the server 120 may ask a question on where the first user 105a gets most of the meals—at home, restaurant, community kitchen, etc. which allows the server 120 to provide strategies for improving purchasing habits, cooking style and also direct them to local community resources. In another example, the server 120 may also ask a question about the favorite meat (e.g., chicken, beef, pork, fish, etc.) of the first user 105a. This would allow the server 120 to identify simple, healthy recipes that can help the user cook the foods he or she likes in a healthier way. Accordingly, the text messages sent to the first user 105a dependent on the responses provided to the previous questions asked by the server 120, are based on the unique circumstances and preferences of the first user 105a, and are therefore customized for the first user 105a.

At step 13, the server 120 determines whether it is time to send the next text message to the first user 105a. For example, the server 120 may check the user preferences, e.g., a preferred schedule (date, time etc.) to receive messages, to determine whether it is time to send the next message. At step 14, the server 120 sends the next text message to the user. In some embodiments, the next text message can be an open ended type interaction, i.e., an interaction to which the first user 105a is not required to respond. At step 15, the first user 105a (in this example) responds by sending a text message including the user's response. At step 16, the server 120 sends the next text message, e.g., information type message to the first user 105a. For example, the text message sent at step 15 can include information relevant to the health coaching program. In some embodiments, the response received from the first user 105a at step 15 may not have a bearing on determining the text message to be sent at step 16 since the text message of step 14 sent to the first user 105a is an open ended type interaction. That is, the text message of step 16 may be sent to the user regardless of whether the first user 105a responded to text message of step 14, and regardless of what the response from the first user 105a contained if the first user 105a responded.

The interactions between the first user 105a and the server 120 can continue for a specified period of time, e.g., for the period of the campaign program defined by the campaign provider, until the first user 105a achieves the health goal, or until the first user 105a decides to quit the campaign program. In some embodiments, the campaign program encourages a particular behavior in the user when the user performs a set of tasks for an extended period. For example, to achieve a health goal such as exercising an hour a day for 3 months, the user may have to perform a set of tasks every day for 3 months which is considered to encourage a particular behavior in the user.

Note that the interactions illustrated in sequence diagram 200 may be altered in various ways. For example, the order of the interactions may be rearranged, substeps may be performed in parallel, illustrated interactions may be omitted; other interactions may be included, etc. For example, the steps 1-5 for setting the health goal may be omitted where the first user 105a specifies the health goal in other ways, such as via a website of the campaign program or by sending an email to the campaign provider. In another example, the number of interactions for setting the health goal may be greater or less than the number of interactions depicted in the sequence diagram 200. In yet another example, the step 11 of determining whether to send the next text message may be performed before sending any or every text message to the first user 105a. In still another example, the type of text messages sent in the interactions can be different—the text message of step 9 can be information type text message, the text message of step 12 can be response type text message, etc.

Figure 3A:
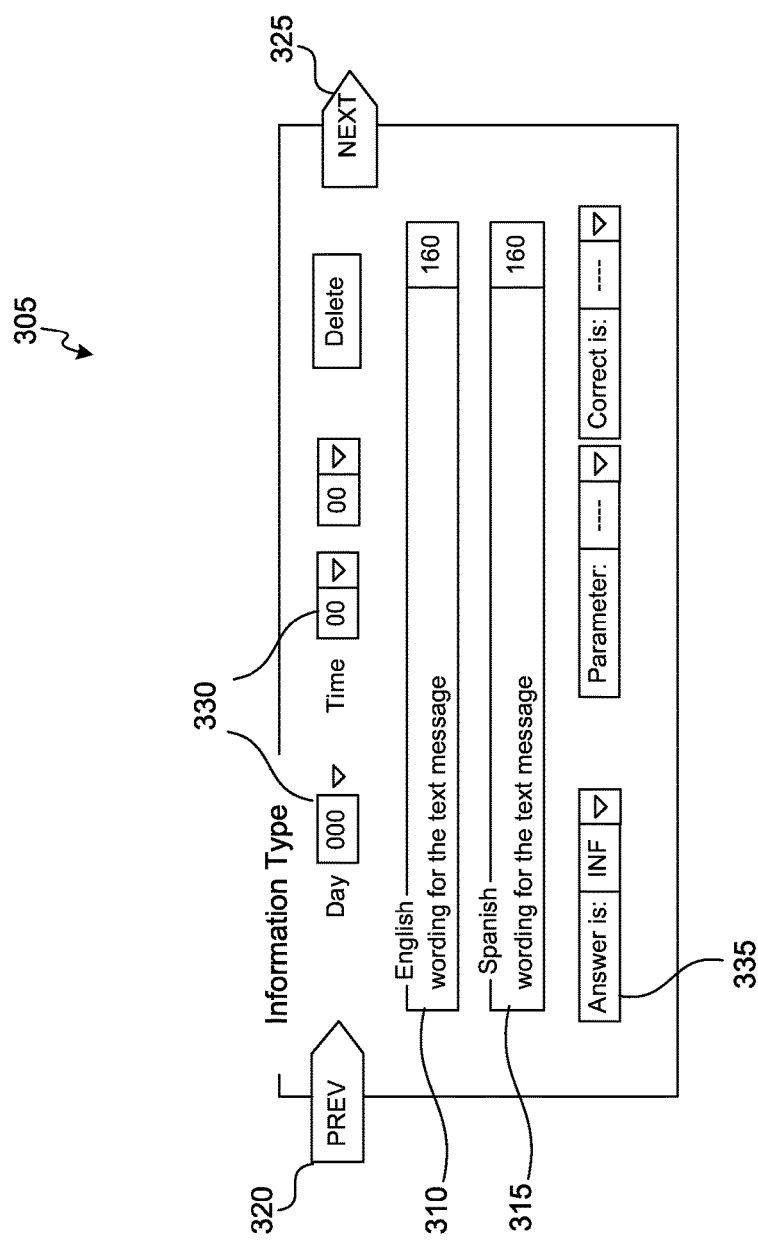
FIGS. 3A, 3B and 3C illustrate interaction components of various types for generating text messages of a campaign program.
Figure 3B:
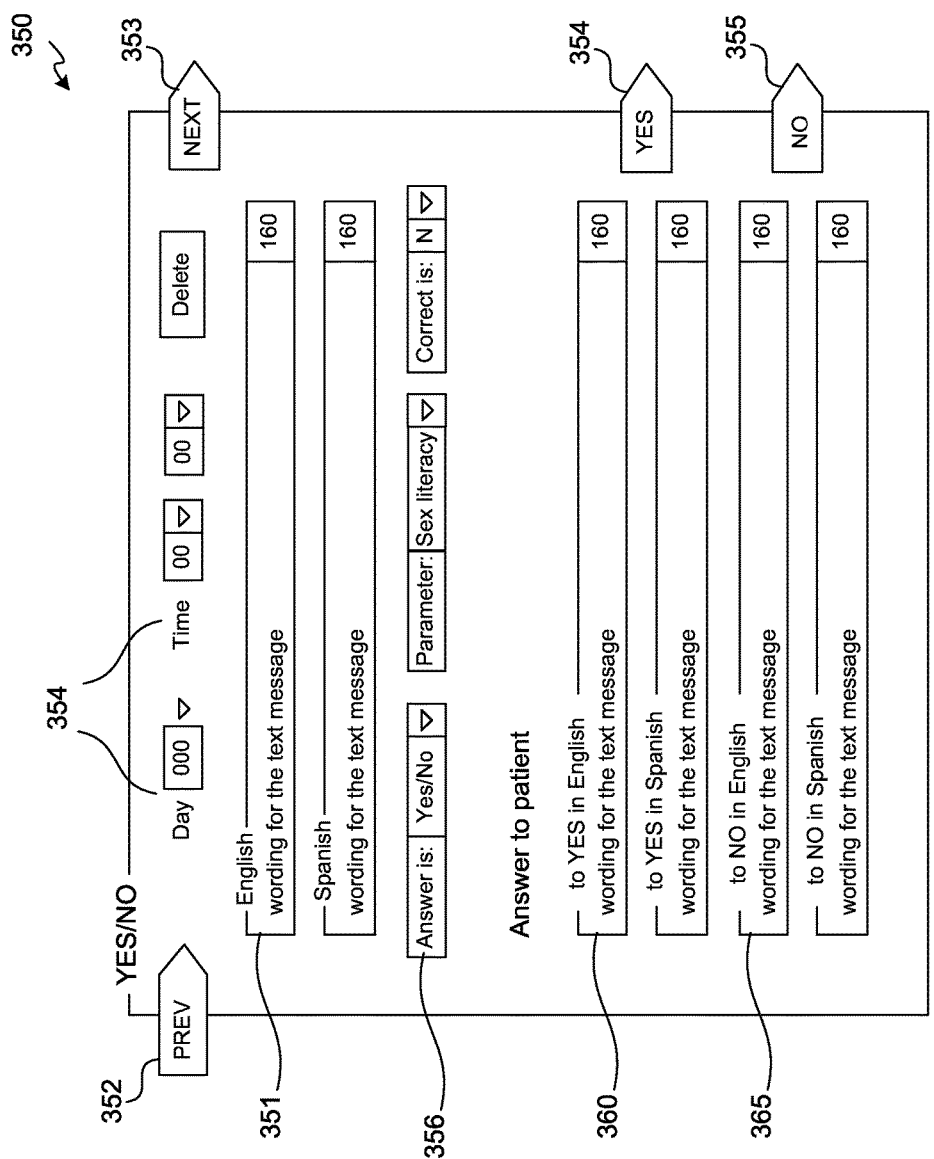
Figure 3C:
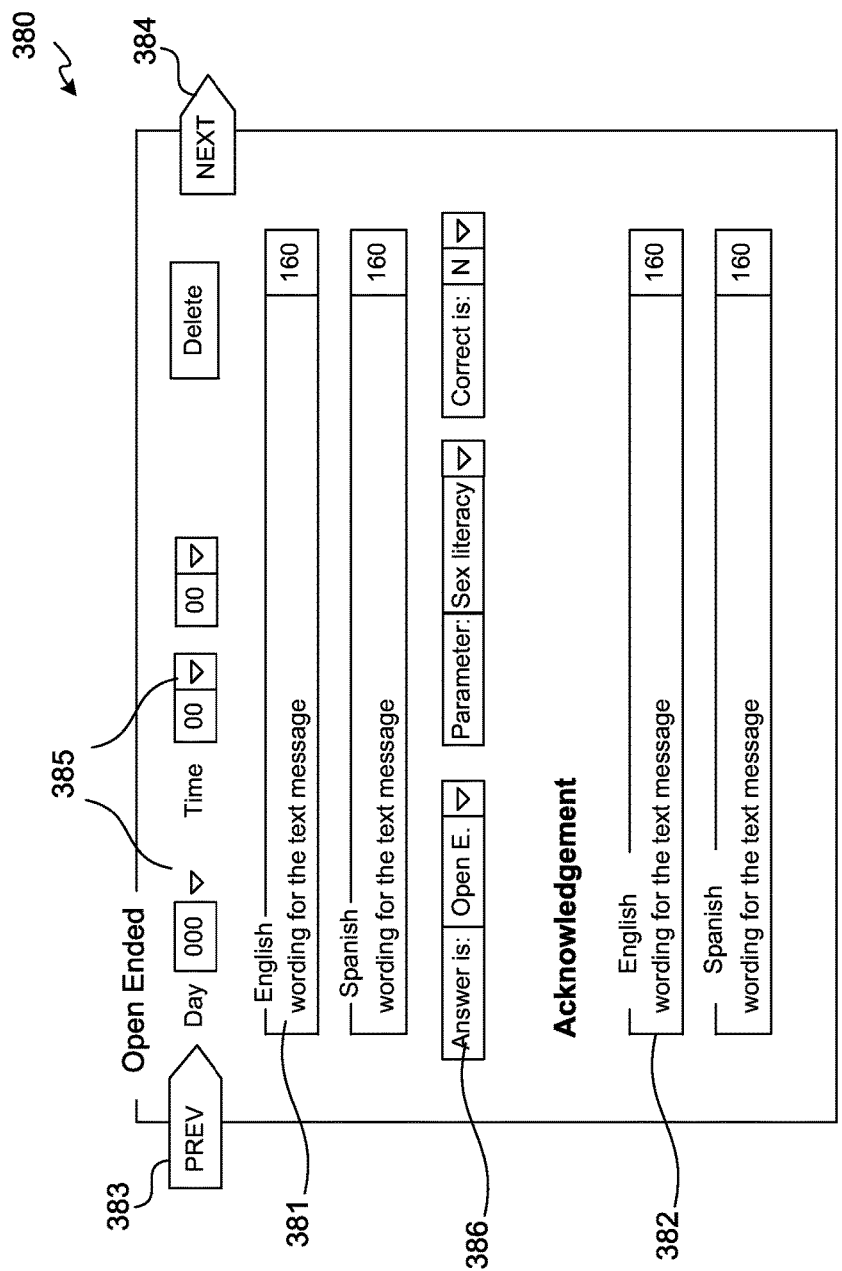

In some embodiments, the above interactions of the campaign program can be created using a campaign creation tool, which is described in further detail with reference to FIG. 4. In some embodiments, the campaign creation tool 400 is a software application that provides a GUI for creating campaign programs. The campaign creation tool 400 provides an interaction component of any of various types, that can be used to generate the interactions of the server 120 with the first user 105a. FIGS. 3A, 3B and 3C illustrate interaction components of various types for generating text messages of a campaign program. The interaction component represents a type of text message generated by the server 120 for the first user 105a. The interaction component can be of three types—(i) "No Answer" type 305 (information-only type): a text message that does not require an answer from the first user 105a, (ii) "Answer" type 350 (response type): a text message that requires an answer from the first user 105a, and (iii) "Open Ended" type 380: a text message for which the user may or may not reply and if the user replies, the response can be of any format.

Each of the interaction components includes a message section that stores the wording of the text message to be sent to a user such as first user 105a. Each of the interaction components can include one or more entry links and one or more exit links. An entry link of a particular interaction component identifies (or is linked from) a prior interaction component from which the particular interaction follows in the sequence of interactions. An exit link of a particular interaction component identifies (or is linked to) a next interaction component that follows the particular interaction in the sequence of interactions. The entry link of some of the interaction components in a campaign program can be null. For example, an entry link of a first interaction component of the campaign program can be null. Similarly, the exit link of some of the interaction components can be null. For example, an exit link of a last interaction component of the campaign program can be null.

Some the interaction components can also include a scheduling component that is used to configure the schedule, e.g., date, time, frequency, etc., for sending the corresponding text message. In some embodiments, if no scheduling is specified, then the text message of the corresponding interaction component can be sent on a schedule determined by the campaign program. For example, such non-scheduled interactions can happen right after the preceding interaction.

Some of the interaction components can also include an acknowledgement section that stores the wording of the response sent to the user right after a response is received from the user. A text message can include a specified maximum number of characters. In some embodiments, a text message includes up to 160 characters. The interaction components can also include a length indicator that indicates the number of characters used and/or still available to be used by the wordings of the text message.

The text messages can be sent in various languages. In some embodiments, the interaction component stores the wordings of the text message in various languages. A user creating the campaign program, e.g., a campaign manager or a campaign provider, can input the wordings in various languages. In some embodiments, the campaign manager can input the wordings of the text message in one language, e.g., English, and the interaction component automatically translates the wordings into other languages. The campaign manager may further edit the translated wordings if preferred. In some embodiments, the interaction component stores the wordings of the text message in one language, e.g., English, and the wordings are automatically translated into a language preferred by the first user 105a when the text messages are sent to the first user 105a.

FIG. 3A illustrates an information-only type interaction component 305. The information-only type interaction component 305 includes a type identifier 335 that identifies the type of the interaction component. The information-only type interaction component 305 includes a first message section 310 that stores the wordings of the text message to be sent to a user, e.g., first user 105a in a first language, e.g., English. The campaign manager or the campaign provider can input these wordings into the first message section 310. The information-only type interaction component 305 also includes a second message section 315 that stores the wordings of the text message in another language, e.g., Spanish. The information-only type interaction component 305 includes an entry link 320 that specifies the preceding interaction from which the interaction component 305 follows. The information-only type interaction component 305 includes an exit link 325 that specifies the next interaction which follows the interaction component 305. The information-only type interaction component 305 includes a scheduling component 330 that stores the schedule according to which the text message is sent to the first user 105*a*. The campaign manager or the campaign provider can input the values of the scheduling component 330 based on the preferences of the first user 105*a*.

FIG. 3B illustrates a response type interaction component 350. Similar to the information-only type interaction component 305, the response type interaction component 350 includes a type identifier 356 that identifies the type of the interaction component, a message section 351 that stores the wordings of the text message to be sent to the first user 105*a*, a scheduling component 354 that stores the schedule according to which the text message is sent to the first user 105*a*, an entry link 352 that specifies the preceding interaction from which the interaction component 350 follows.

The text message of interaction component 350 requires the first user 105*a* to respond to the message, e.g., as a "Yes" or "No." In some embodiments, the interaction component acknowledges the first user 105*a* upon receiving the response from the first user 105*a*. The response type interaction component 350 includes an acknowledgement section that store the wordings of the text message for acknowledging the response of the first user 105*a*. A first acknowledgement section 360 stores the wordings of the text message for acknowledging a "Yes" response from the first user 105*a*. A second acknowledgement section 365 stores the wordings of the text message for acknowledging a "No" response from the first user 105*a*.

The response type interaction component 350 includes three exit links: a first exit link 353 that specifies the next interaction component which follows the interaction component 350 regardless of a "Yes" or "No" response from the first user 105*a*, a second exit link 354 that specifies the next interaction which follows the interaction component 305 upon receiving a "Yes" response from the first user 105*a*, and a third exit link 355 that specifies the next interaction which follows the interaction component 305 upon receiving a "No" response from the first user 105*a*. The campaign provider or the campaign manager can decide the flow of interactions, that is, either to use the first exit link 353 or the second and third exit links 354 and 355. If the campaign manager or the campaign provider decides that the next interaction should not be based on the response from the first user 105*a* to the interaction component 350, the first exit link 353 is used. On the other hand, if the campaign manager or the campaign provider decides that the next interaction should be based on the response, the second and third exit links 354 and 355 are used.

The interaction component 350 expects to receive a response in the form of "Yes" or "No". However, various other forms of response can be received. For example, the users may be asked reply with (i) a "True" or "False" response, (ii) a user selection of one of multiple choices provided in the text message, (iii) a value within a given range, etc. In some embodiments, each of the possible answers to the question presented by the text message of the response type interaction component 350 can have an associated exit link.

FIG. 3C illustrates an open ended type interaction component 380. Similar to the response type interaction component 350, the open ended type interaction component 380 includes a type identifier 386 that identifies the type of the interaction component, a message section 381 that stores the wordings of the text message to be sent to the first user 105*a*, a scheduling component 385 that stores the schedule according to which the text message is sent to the first user 105*a*, an entry link 383 that specifies the preceding interaction component from which the interaction component 380 follows. The open ended type interaction component 380 includes an acknowledgement section 382 that stores the wordings of the text message for acknowledging the response of the first user 105*a*. In some embodiments, the open ended type interaction component 380 does not expect the response to be in any particular format.

The open ended type interaction component 380 includes an exit link 384 that specifies the next interaction component which follows the interaction component 380. In some embodiments, the exit link 384 may be linked to another interaction component based on the response received from the first user 105*a* contains. In some embodiments, the exit link 384 may be linked to another interaction component regardless of what the response received from the first user 105*a* contains.

Figure 4:
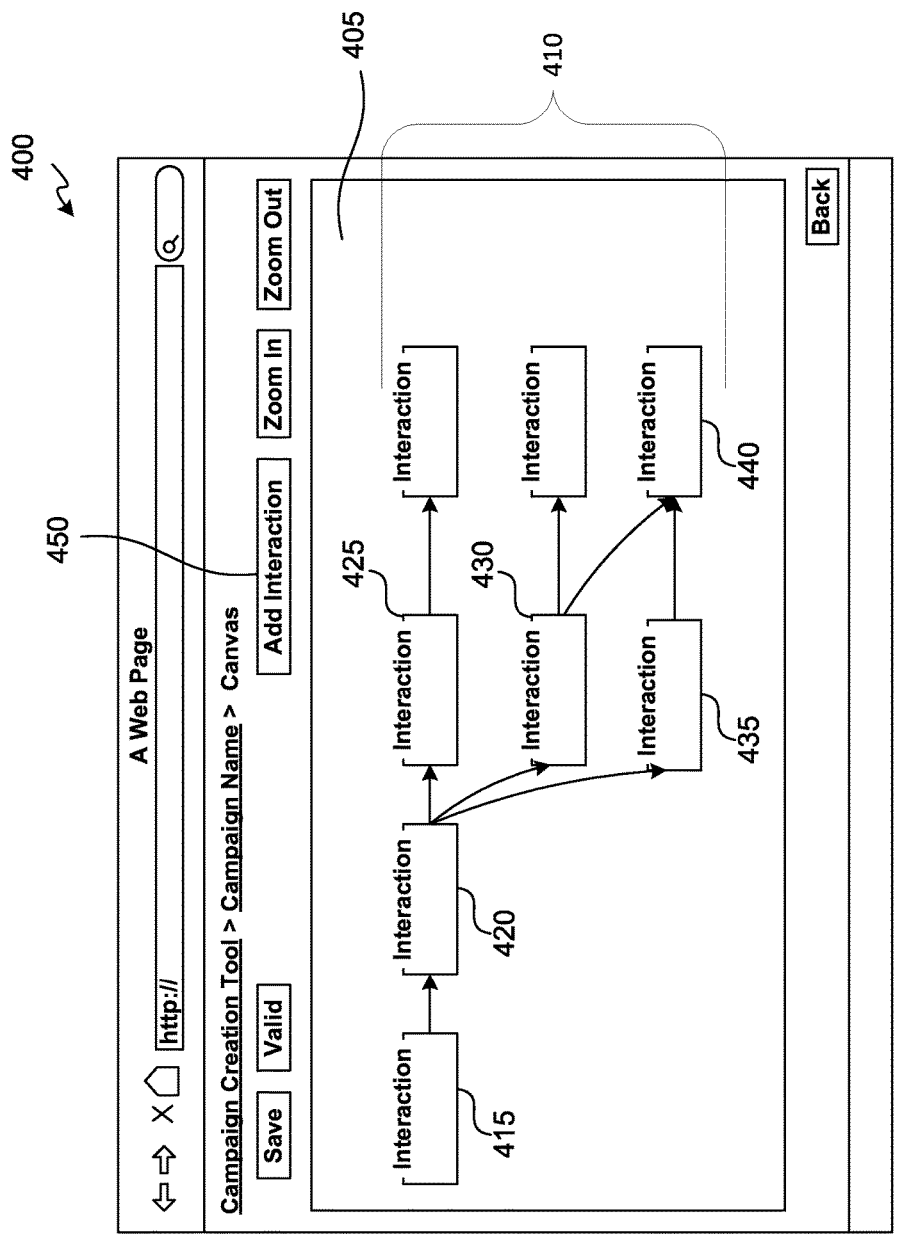
FIG. 4 illustrates a campaign creation tool for creating a campaign program.

FIG. 4 is a block diagram illustrating a campaign creation tool 400 for creating a campaign program. In some embodiments, the campaign creation tool 400 can be used to generate campaign programs that can be implemented in the environment 100 of FIG. 1. The campaign creation tool 400 is an interaction component based tool, where a campaign program is created by generating various interaction components 410 of various types, such as the interaction components described with reference to FIG. 3, and linking the interaction components 410 in a sequence. A user, such as a campaign manager or a campaign provider, who conducts the campaign program may use the campaign creation tool 400 to create the campaign program.

In some embodiments, the campaign creation tool 400 provides a GUI. The campaign creation tool 400 includes a canvas 405 where the interaction components 410 can be created and linked to each other in a sequence. The campaign manager can create an interaction component by using interaction component creation tool 450. For example, when the campaign manager selects the interaction component creation tool 450 an interaction component, e.g., interaction component 415, is added in the canvas 405. After adding the interaction component 415, the campaign manager may input various data into the interaction component 415, as described with reference to FIG. 3. For example, the campaign manager may input data, including a wording of the specific message to be sent as a text message, a schedule of the text message, an entry link that specifies an interaction component that precedes the interaction component 415, which is null for interaction component 415 since it is the first interaction component of the campaign program, an exit link that specifies interaction component 420 as the next interaction component of the sequence which follows the interaction component 415, etc.

The campaign program manager can create various such interaction components 410 for various messages to be sent to the user, such as first user 105*a*, participating in the campaign program. In some embodiments, the interaction components 410 represent a complete set of text messages of the campaign program. However, the specific text messages that is sent to the first user 105*a* depends on the responses received from the first user 105*a*. Further, in some embodiments, the interaction components 410 can also include auxiliary messages that are not directly related to the campaign program. The auxiliary messages can include (a) an unrequested response message—a text message sent to the first user 105*a* when the server 120 receives an unexpected response from the first user 105*a*, (b) opt out message—a text message to inform the first user 105a how to opt out from the campaign program, (c) opt out acknowledgement message—a text message to inform the first user 105a that the first user 105a has successfully opted out, (d) opt in acknowledgement message—a text message to inform the first user 105a that the first user 105a has successfully opted in, etc.

After creating the interaction components 410, the campaign manager may link the interaction components 410 to one another in a sequence according to which the text messages are to be sent to the first user 105a. The linking of interaction components 410 in a sequence forms a decision tree which is used in determining the next interaction component, or a text message corresponding to the next interaction component, that follows the current interaction component. The linking includes connecting the exit link of one interaction component to an entry link of the other interaction component in the canvas 405. In some embodiments, an interaction component can be represented as a data structure, e.g., a data object, in the server 120, and the text message, entry and exit links, scheduling component, interaction component type, etc. of the interaction component can be represented as attributes of the object. The object can have methods to operate on these attributes to set or get values of the attributes. For example, when an exit link of a first interaction component is linked to an entry link of a second interaction component in the GUI, the exit link attribute of the object corresponding to first interaction component can be updated to contain the name of the object corresponding to the second interaction component as the attribute value. Similarly, the entry link attribute of the object corresponding to second interaction component can be updated to contain the name of the object corresponding to the first interaction component as the attribute value.

Recall from FIG. 3B that an interaction component can have multiple exit links, one for each possible answer to the question presented by the text message of the interaction component. For example, the interaction component 420 has three exit links, a first exit link connected to an entry link of interaction component 425, a second exit link connected to an entry link of interaction component 430, and a third exit link connected to an entry link of interaction component 435. The linking of the interaction component 420 to three different interaction components indicates that if the response from the first user 105a to the question posted by the text message of interaction component 420 includes a first answer, the next text message to be sent to the first user 105a is a text message corresponding to the interaction component 425. Similarly, if the response includes a second answer or third answer, the next text message to be sent to the first user 105a is a text message corresponding to the interaction component 430 or 435, respectively.

In some embodiments, more than one interaction component may be linked to a particular interaction component. This can mean that the particular component appears in more than one sequence. In the GUI, more than one interaction component may be linked to the particular interaction component by connecting the exit links of the one or more interaction components to an entry link of the particular interaction component. For example, the exit links of interaction components 430 and 435 are connected to an entry link of interaction component 440.

In some embodiments, the exit link of the interaction component may be null, that is, the interaction component may not be connected to any interaction components further in the sequence. For example, a last interaction component in the campaign program such as interaction component 440 may not be further connected to other interaction components. The GUI allows the interaction components 410 to be moved around in the canvas 405, and to link or unlink the interaction components 410 with one another.

The decision tree formed by linking various components enables the server 120 to determine the next text message to be sent to the user. Further, since different users can respond with different answers, the decision tree helps in determining the text messages that are more relevant to the particular user and therefore, facilitates customizing the text messages for a particular user.

The campaign creation tool 400 performs a number of validations on the interaction components 410. In some embodiments, the validations performed can depend on the type of the interaction component. In some embodiments, the interaction components 410 added to the canvas 400 is considered to be valid if: (a) the linkage entry option for each interaction component has been linked (except for the first one which does not need entry linkage); (b) if an interaction component has different exit options based on the user's response, all of them are linked or none of them are linked, and (c) the linkage flow between interaction components is compliant with the schedule set in the interaction components, e.g., an interaction component set for day 4 at 5 pm cannot precede an interaction set for day 4 at 3 pm, etc.

After the campaign program is validated, the campaign creation tool 400 allows the campaign manager to store the campaign program and send it to the server 120 for deployment. In some embodiments, the campaign creation tool 400 generates an executable code for the campaign program in a format that can be executed by the server 120.

Further, the campaign creation tool 400 can be a web-based tool that can be accessed via a web browser, or can be an application that can be accessed on a computing device, including a laptop, a desktop, a mobile phone, a smartphone, a tablet PC, etc. In some embodiments, the campaign creation tool 400 can be accessed on the computing device by executing a set of binary code representing the campaign creation tool 400.

Figure 5:
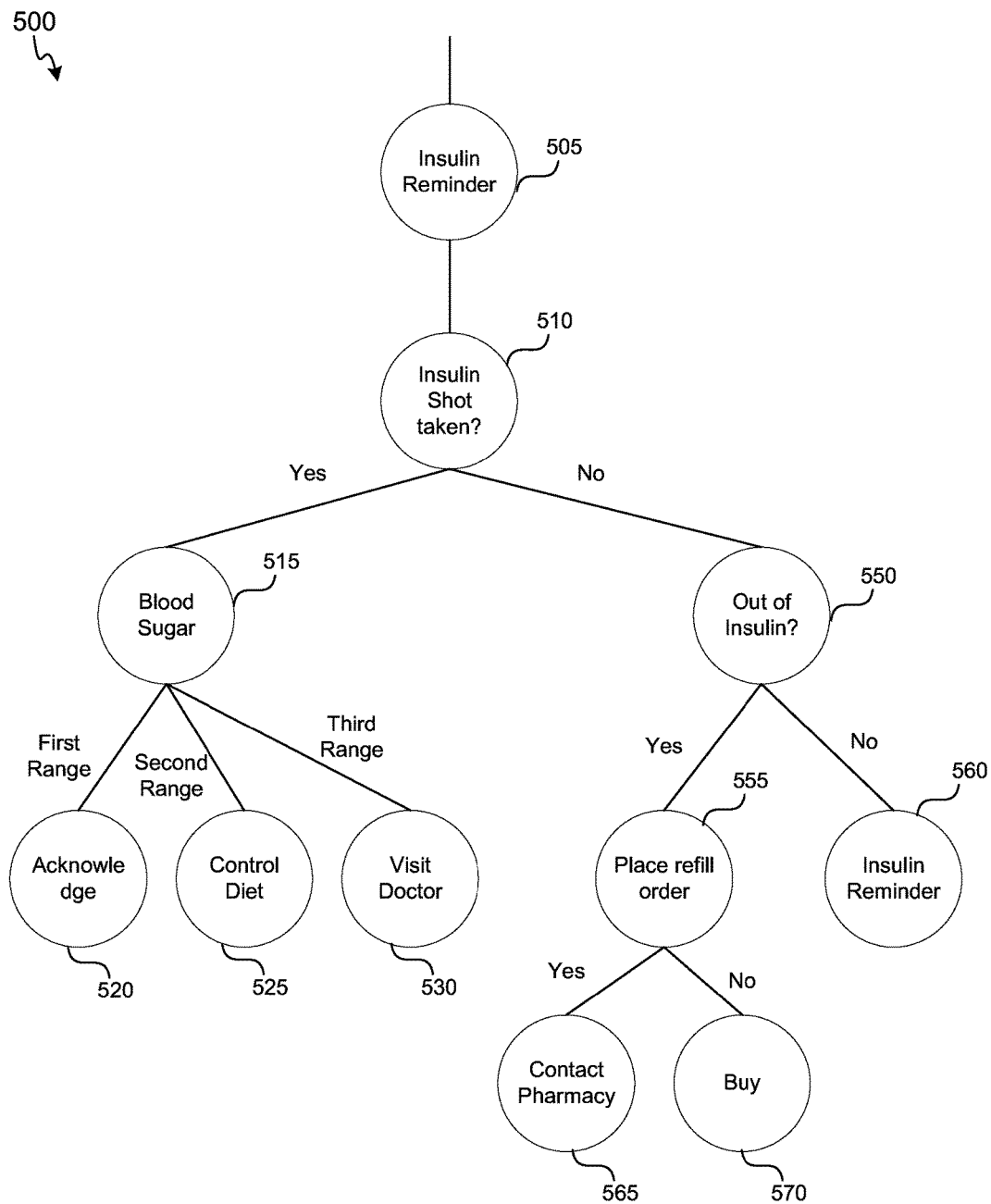
FIG. 5 illustrates an example of a decision tree (data structure) used to determine the text messages to be sent to an individual participating in a diabetes management campaign program.

FIG. 5 illustrates an example of a decision tree (data structure) 500 that can be used to determine the sequence of text messages to be sent to an individual participating in a diabetes management campaign program. In some embodiments, the decision tree 500 can be created by linking various interaction components corresponding to the messages to be sent to an individual participating in the diabetes management campaign program in the campaign creation tool 400, e.g., as described with reference to FIG. 4. The decision tree 500 can be a portion of a larger decision tree that can be generated for the diabetes management campaign program. In some embodiments, the decision tree 500 can be employed in the environment 100 for sending text messages to the users 105a-c regarding the diabetes management campaign program by the server 120.

At node 505, the server 120 sends a text message reminding a user, e.g., first user 105a, to take an insulin shot. After a certain period, e.g., based on the preferred schedule by the first user 105a to receive the next message, at node 510, the server 120 sends a text message asking the first user 105a whether the first user 105a has taken the insulin shot. The text message prompts the first user 105a to respond with a "Yes" or "No."

If the first user 105a responds with a "Yes," the server 120 determines from the decision tree 500 that a text message corresponding to node 515 is to be sent to the first user 105a. For example, the text message corresponding to the node 515 can be a text message asking the first user 105a to report his blood sugar level. In some embodiments, the server 120 can present certain sample sugar level ranges in the text message from which the first user 105a can choose a range corresponding to the first user's 105a blood sugar level and respond with the chosen range as a text message. In some embodiments, the first user 105a can send the actual reading of the sugar level in the text message.

The response to a text message corresponding to the node 515 can have one of three possible answers. The server 120 sends the next text message, e.g., a text message corresponding to one of the three nodes 520, 525 and 530 based on the answer in the received response. For example, upon receiving a response having the blood sugar level of the first user 105a, the server 120 determines a range to which the first user's 105a blood sugar level corresponds. If the blood sugar level corresponds to a first range, at node 520, the server 120 sends a text message, for example, acknowledging the first user's 105a effort in maintaining his blood sugar level. If the blood sugar level corresponds to a second range, at node 525, the server 120 sends a text message, for example, recommending the first user 105a to control his diet in order to maintain the blood sugar level. If the blood sugar level corresponds to a third range, at node 530, the server 120 sends a text message, for example, recommending the first user 105a to visit a doctor to get additional treatments for controlling the blood sugar level.

Referring back to node 510, if the first user 105a responds with a "No," the server 120 determines from the decision tree 500 that a text message corresponding to node 550 is to be sent to the first user 105a. For example, the text message corresponding to the node 550 can be a text message asking the first user 105a if the first user 105a is out of insulin. The response to a text message corresponding to node 550 can have one of two possible answers. The server 120 sends the next text message, e.g., a text message corresponding to one of the two nodes 555 and 560, based on the answer in the received response. For example, if the response from the first user 105a is a "Yes", at node 555, the server 120 sends a text message asking whether the first user 105a wishes to place an order to refill his insulin shots. If the response is a "No," at node 560, the server 120 sends a text message reminding the first user 105a to take the insulin shot.

Referring back to node 555, the response to a text message corresponding to node 555 can have one of two possible answers. The server 120 sends the next text message, e.g., a text message corresponding to one of the two nodes 565 and 570, based on the answer in the received response. For example, if the response is a "Yes," the server 120 sends the next text message asking the user to contact the pharmacy to place a refill order. If the response is a "No," the server 120 sends the next text message asking the first user 105a to buy the insulin shot. Accordingly, the decision tree 500 enables the server 120 to determine a sequence of the text messages to be sent to a user participating in the diabetes management campaign program. Further, the decision tree 500 allows the text messages to be sent to the users be customized to the user (or a group of similar users) based on the responses received from the user.

As described above, the campaign program is designed as an interactive program where a sequence of text messages sent to the user are customized to the user. That is, the next text message in the sequence sent to the user is based on a response received from the user for a prior text message in the sequence. In some embodiments, the participant can initiate a particular sequence by sending a particular message to the server 120. The campaign program can have certain keywords, e.g., "HELP," "EXIT," that when sent by the participant in a message triggers a specific sequence that otherwise may not occur in the campaign program or that may occur at a different time or in a different portion of the current sequence. For example, in the above diabetes management campaign program, consider that the participant is at node 510, where the participant is expect to respond with a "Yes" or "No" to the question "Insulin shot taken?" If the participant sends a "Yes" or "No," the next step in the sequence can be node 515 or 550. However, if the user sends the keyword "EXIT," the message can cause the server 120 to send a different sequence of messages other than node 515 or 550, e.g., a message acknowledging participant's intention to quit, a message asking the reason to quit, etc. Accordingly, the sequence of messages exchanged between the server 120 and the participant can also be based on certain keywords in the message sent by the user.

In some embodiments, the sequence of the text messages sent to the user is also determined based on other data, such as clinical data, demographic data, participant's profile data. For example, clinical data can include health related data of a participant such as blood sugar level; demographic data can include or be based on age, gender, ethnicity, etc. of a number of participants; participant's profile data can include a particular participant's age, gender, lifestyle habits, etc. Such other data may be obtained from any of various sources, e.g., medical institutions, doctors, patients, participants, or other third-parties who provide such data.

The campaign manager can create different interaction sequences for a campaign program based on the above data, and store them as different sequences of the campaign in the storage facility 125. For example, for the above diabetes management campaign program, the campaign manager can create a first interaction sequence for male participants and a second interaction sequence for female participants. In another example, the campaign manager can create different interaction sequences for groups of participants having different diets. In yet another example, the campaign manager can create different interaction sequences for participants of different age groups, different ethnicities, different lifestyle habits, e.g., athletes, etc.

The campaign manager can use the campaign creation tool 400 to create the different sequences as described at least with reference to FIG. 4. At least some of the interaction components that make up a particular message sequence can be different for two different interaction sequences of a campaign program. The different interaction sequences can be stored as separate interaction sequences of the campaign program in the storage facility 125.

In some embodiments, the storage facility 125 provides a library of interaction sequences. The campaign manager can search the library for one or more interaction sequences, select one of them and use the selected interaction sequence for conducting the campaign. In some embodiments, after selecting a particular interaction sequence from the search results, the campaign manager can further customize the interaction sequence to suit the needs of a specific campaign program. For example, the campaign manager can create an interaction sequence for participants with vegan diet by customizing an existing interaction sequence generated for participants with vegetarian diet. The customizing can include any of adding an interaction component, such as the interaction components of FIG. 4, removing an interaction component, changing the message of the interaction component, changing the entry link of an interaction component, changing the exit link of an interaction component, etc.

The campaign creation tool 400 allows the campaign manager to search the library for one or more interaction sequences based on various search criteria, such as clinical data, demographic data, e.g., a particular age group, a particular ethnic group, particular blood sugar level, gender of participants etc. The campaign manager can also customize a particular interaction sequence using the campaign creation tool.

Figure 6:
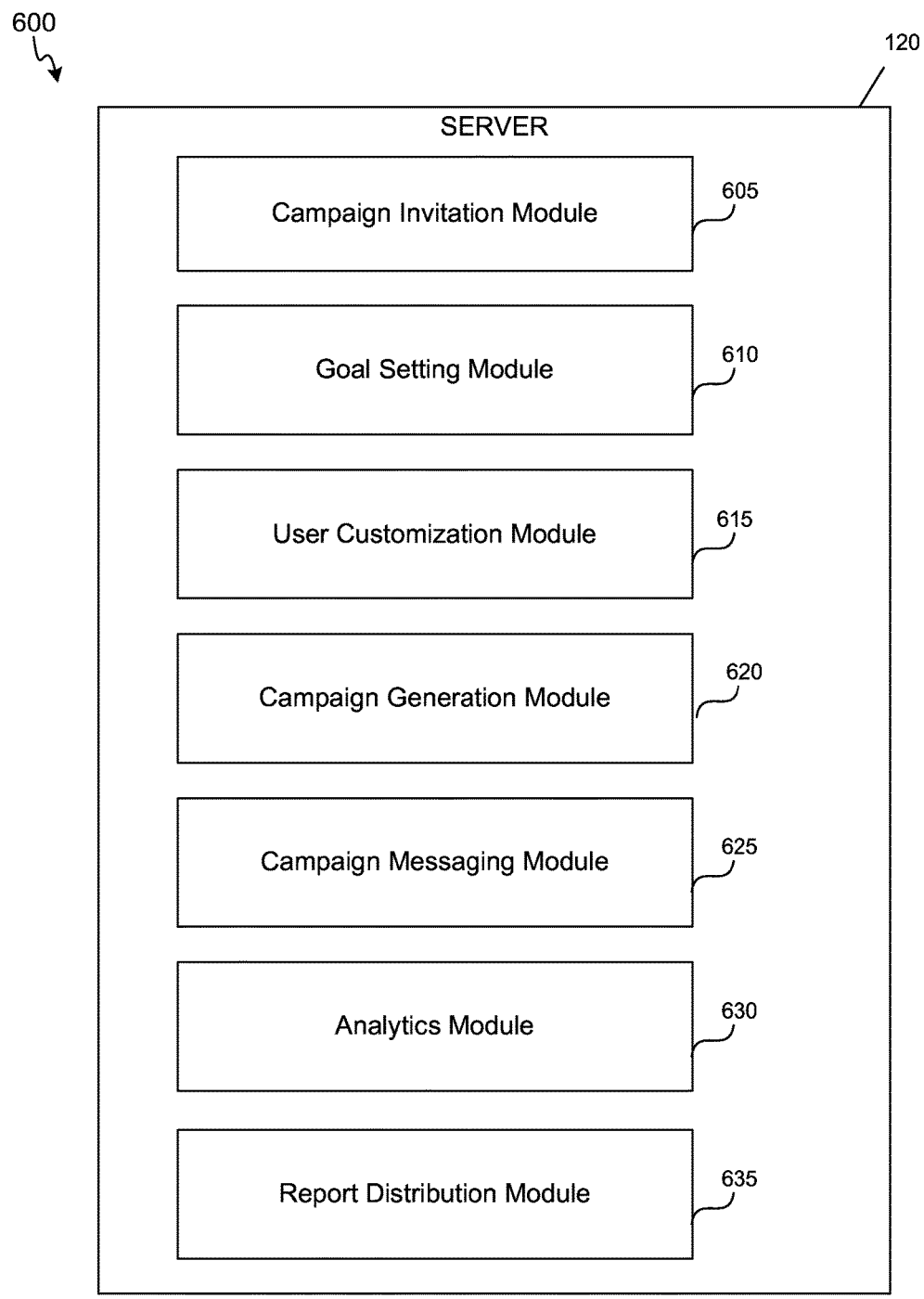
FIG. 6 is a block diagram of a server for executing a text message based campaign program.

FIG. 6 illustrates a block diagram 600 of a server for executing a text message based campaign program. The server 120 facilitates sending text messages related to a campaign program to a set of users 105a-c. The server 120 includes a campaign invitation module 605 that sends text messages to the users 105a-c inviting them to enroll for a particular campaign program. In some embodiments, the invitation text messages may be sent to all users 105a-c in a batch, e.g., as a group text message. The invitation text messages may be sent to mobile devices associated with the users 105a-c. An example of a mobile device can include a mobile phone, a smartphone, a tablet PC, a laptop, etc.

The campaign invitation module 605 also receives the responses to the invitations from the users 105a-c. The campaign invitation module 605 may identify that some of the users 105a-c are willing to enroll, some do not want to enroll and some of them have not responded to the invitations. The campaign invitation module 605 identifies the responses and processes them accordingly. Further, the campaign invitation module 605 can also send welcome messages to the users 105a-c that have enrolled, and can also send more details about the campaign program.

The server 120 includes a goal setting module 610 that exchanges text messages with the users 105a-c for identifying the goals the users 105a-c want to achieve as part of the campaign program. In some embodiments, the goal setting module 610 can also interact with the users 105a-c to set their goals via emails or website of the campaign program.

The user customization module 615 is configured to receive user preferences from the users 105a-c. The user preferences can include a schedule, e.g., a particular day and time, at which the users prefer to receive the text messages, frequency, etc.

The campaign generation module 620 generates the text messages of the campaign program for the users 105a-c based on their user preferences and their respective goals. In some embodiments, the text messages can be customized for a group of users who are considered to be similar by the campaign program. The text messages can be of various types as described at least with reference to FIGS. 2 and 3.

The campaign messaging module 625 sends the text messages of the campaign program to the users 105a-c in a particular sequence. For the text messages which require an answer from a user, e.g., first user 105a, the campaign messaging module 625 ensures that a next text message is not sent until the first user 105a responds to the text message. Upon receiving the response from the first user 105a, the campaign messaging module 625 analyzes the response, identifies the next text message in the sequence to be sent to the first user 105a based on the response and using the decision tree of the campaign program, as described at least with reference to FIG. 4, and sends the next text message. The campaign message module 625 sends the text messages to the users 105a-c based on the schedule preferred by the users 105a-c.

The interaction between the campaign messaging module 625 and the first user 105a continues for a certain period, e.g., until the campaign program ends, the first 105a achieves the goal, the first 105a opts out, etc.

The server 120 also includes analytics module 630 that generates various statistical data for the campaign programs, including a response rate (RR), a response speed (RS), a response speed in 6 min (RS-5MIN), a drop-off rate (DR), etc. The server 120 includes a report distribution module 635 that generates a report of the statistical data for a particular campaign program and sends the report to the campaign manager or provider of the particular campaign program. In some embodiments, the campaign providers can track how their campaign programs are performing and/or modify certain aspects of the campaign program to enhance the performance of the campaign programs based on the statistical data.

Figure 7:
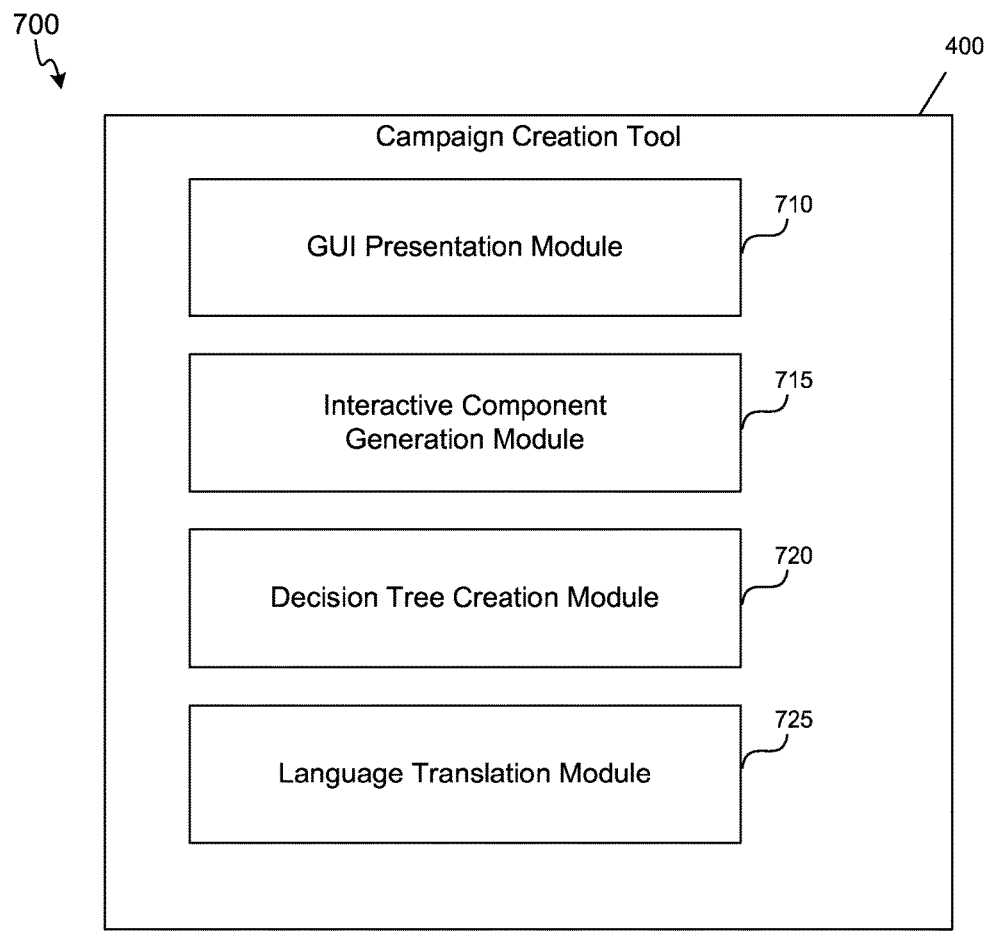
FIG. 7 is a block diagram of a campaign creation tool.

FIG. 7 is a block diagram 700 illustrating a campaign creation tool 400 for generating a campaign program. The campaign creation tool 400 includes a GUI presentation module 710 that renders or presents a GUI of the campaign creation tool 400 at a display of a computer system. The campaign creation tool 400 is an interaction component based tool, where a campaign program is created by generating various interaction components of various types, such as the interaction components described with reference to FIG. 3, and linking the interaction components in a sequence.

The interaction component generation module 715 is used to generate the interaction components. The GUI includes a canvas 405 where the various interaction components representing a complete set of text messages of the campaign program can be created. After creating the interaction components, the interaction components may be linked to one another in a sequence using a decision tree creation module 720. The linking of interaction components in a sequence forms a decision tree which helps in determining the next interaction component (rather a text message corresponding to the next interaction component) that follows the current interaction component. If a question presented to a user by a text message can have more than one possible answer, the next text message to be sent to the user can be different for different answers. Accordingly, the decision tree links a particular interaction component to one or more interaction components for different answers. When the user responds to a particular text message, the response is analyzed and the next message to be sent to the user is determined based on the response and using the decision tree. In some embodiments, the linking includes connecting the exit link of one interaction component to an entry link of the other interaction component in the canvas 405.

The campaign creation tool 400 also includes a language translation module 725 that translates the text messages from a given languages to various other languages. For example, the campaign manager can input the wording of the text message in the interaction component in English, the language translation module 725 can translate the wording from English to other languages, such as Spanish, Mandarin etc. In some embodiments, the text message may be translated from one language to another language when the text message is sent to a user based on the user's preference. In some embodiments, the text message may be translated from one language to other languages when the wording of the text message is input by the campaign manager or provider into the interaction component.

Figure 8:
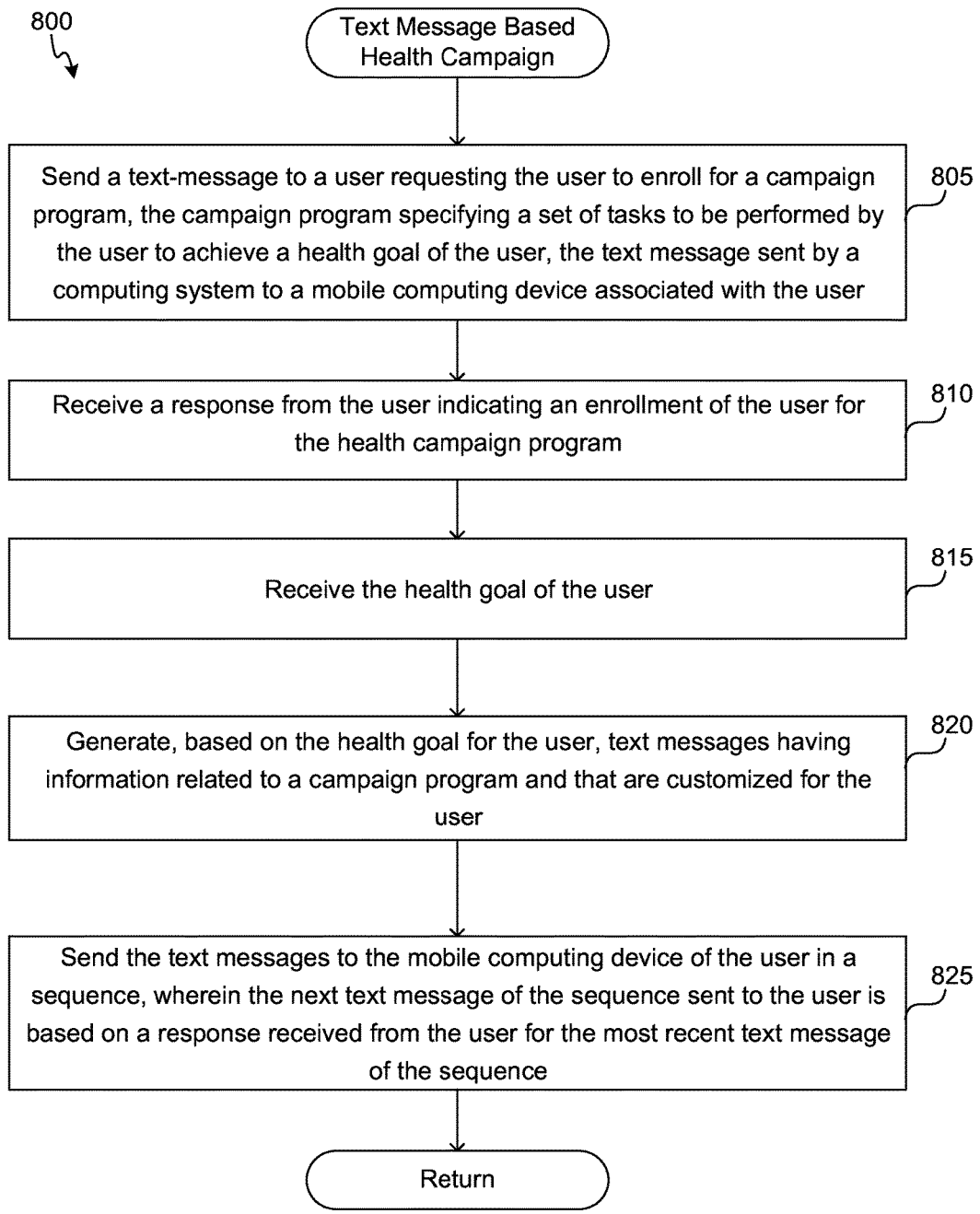
FIG. 8 is a flow diagram of a process of conducting a text message based health campaign.

FIG. 8 is a flow diagram a process 800 of conducting a text message based health campaign. In some embodiments, the process 800 may be implemented in the environment 100 of FIG. 1, and using the system 600 of FIG. 6. At block 805, the campaign invitation module 605 sends a text message to a user requesting the user to enroll for a health campaign program. In some embodiments, the health campaign program is a set of tasks to be performed by the user to achieve a health goal of the user. The text messages are sent to a mobile computing device associated with the user. In some embodiments, the text messages are sent to the mobile device using a messaging service provided by a wireless telecommunications network. The messaging service can be or include SMS, MMS, or another known or convenient messaging service. The text messages can be short text messages or multimedia messages. In some embodiments, the text messages are sent to the mobile device at least partly via a computer network, e.g., the Internet, using applications such as a social networking application.

At block 810, the campaign invitation module 605 receives a response from the user indicating an enrollment of the user for the health campaign program. The user sends the response via a text message from the user's mobile computing device.

At block 815, the goal setting module 610 receives the health goal for the user. The health goal may be received in various ways. For example, the goal setting module 610 can exchange a set of text messages with the user for receiving a health goal for the user. The goal setting module 610 can send multiple health goals to the user and then receive the user's selection of one of the health goals as the user's health goal. In another example, the goal setting module 610 can receive the health goal from the user via email or a website of the health campaign program.

At block 820, the campaign generation module 620 generates a number of text messages having information related to the health campaign program. The text messages are customized for the user and generated based on the health goal for the user.

At block 825, the campaign messaging module 625 sends the text messages to the mobile computing device of the user in a particular sequence. The text messages that are sent to the user can vary depending on the responses received from the user. For example, if a response from the user to a particular question is "Yes," the next text message sent to the user can be different from the text message sent to the user if the response is "No." The sequence is determined using a decision tree, which helps in determining the next text message of the sequence to be sent to the user based on a response received from the user for the most recent text message of the sequence. The interaction between the user and the server 120 continues for a given period, e.g., until the health campaign program ends, the user achieves the health goal, the user opts out, etc., and the process 800 returns.

Figure 9:
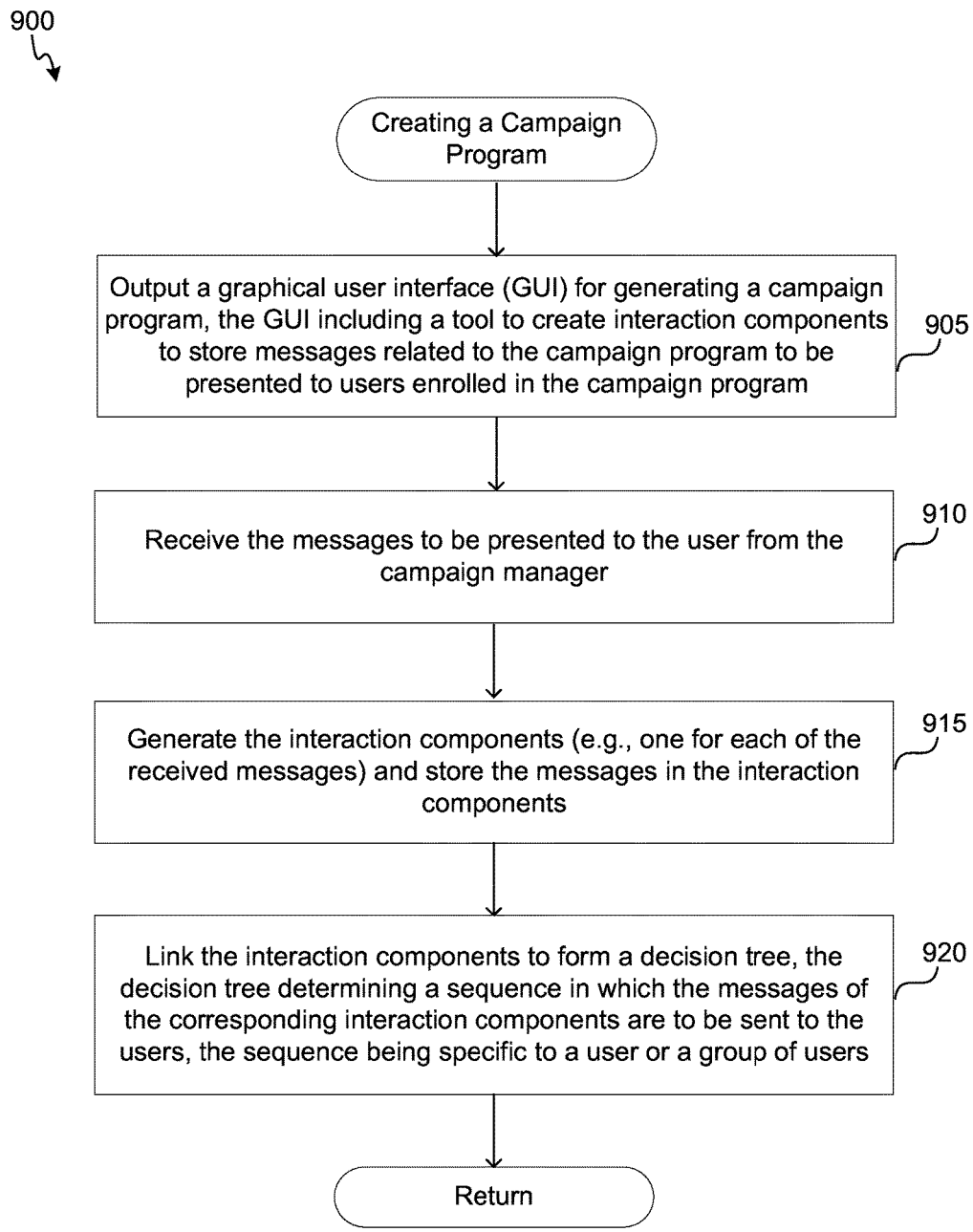
FIG. 9 is a flow diagram of a process for creating a campaign program using a campaign creation tool.

FIG. 9 is a flow diagram of a process 900 for creating a campaign program using a campaign creation tool. In some embodiments, the process 900 may be implemented in the environment 100 of FIG. 1, and using the system 700 of FIG. 7.

At block 905, the GUI presentation module 710 outputs the GUI of the campaign creation tool 400 at an output device associated with a computer system, e.g., of a campaign provider or a campaign manager of the campaign program. The campaign creation tool 400 is an interaction component based tool, where a campaign program is created by generating various interaction components of various types, such as the interaction components described with reference to FIG. 3, and linking the interaction components in a sequence. The interaction components store the messages of the campaign program that are to be presented to multiple users, e.g., as text messages.

At block 910, the interaction component generation module 715 receives the messages related to the campaign program from the campaign manager. The messages can include at least one of information related to the campaign program or questions requesting a response from the users.

At block 915, the interaction component generation module 715 generates the interaction components, e.g., one for each of received messages, and stores the messages in the corresponding interaction components. Each of the interaction components has a specific message that presents at least one of a specific information item regarding the campaign program or a specific question requesting a response from the users. In some embodiments, the campaign manager can further configure the properties of the interaction components, e.g., interaction component type, schedule, etc.

The campaign manager can link the interaction components to one another, e.g., in a sequence the messages have to be sent. At block 920, the decision tree creation module 720 generates a decision tree based on the linking of the interaction components, and the process 900 returns. The decision tree identifies the sequence in which the text messages of the corresponding interaction components are to be sent to the users. In some embodiments, the decision tree identifies, for each of the users, a particular message in the sequence to be sent to the user for a particular response received from the corresponding user. In some embodiments, the decision tree helps in keeping the text messages more customized and relevant to each of the users participating in the campaign program.

Figure 10:
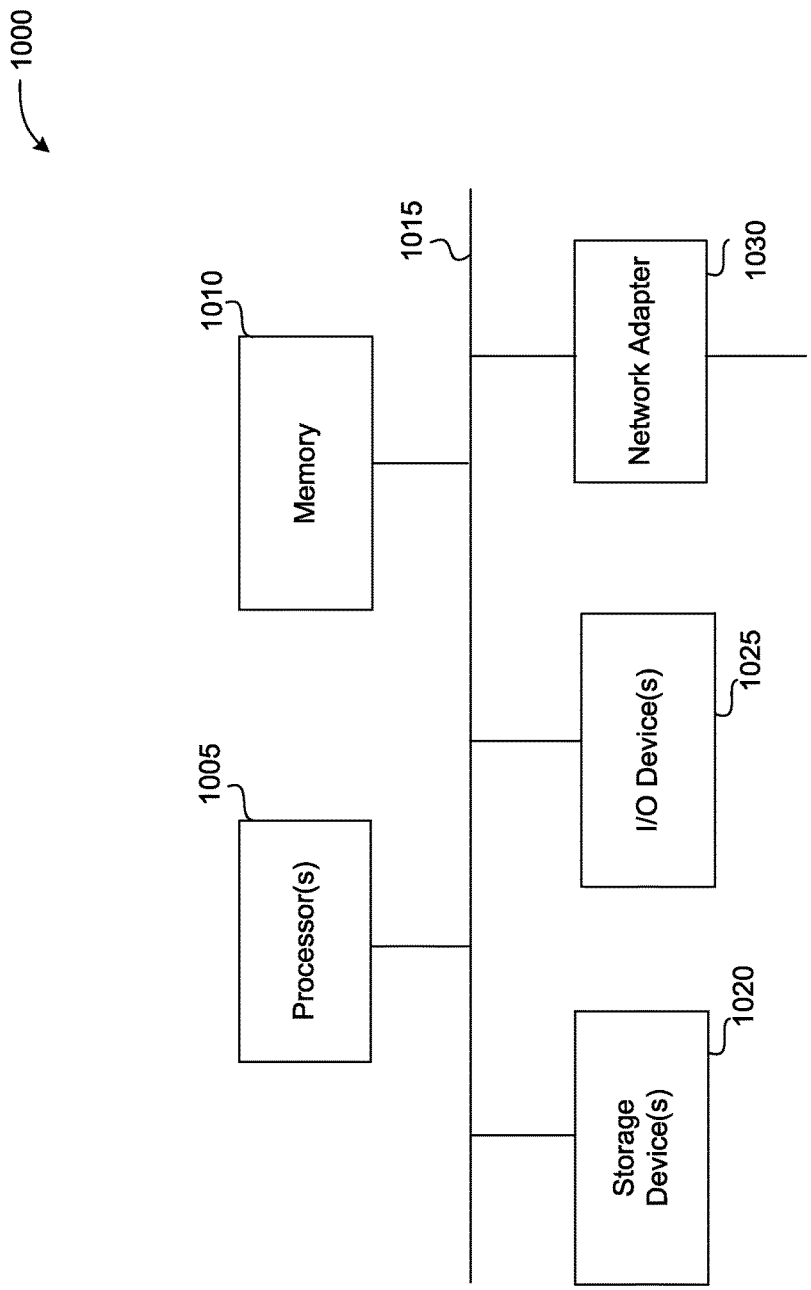
FIG. 10 is a block diagram of a computer system as may be used to implement features of some embodiments of the disclosed technology.

FIG. 10 is a block diagram of a computer system as may be used to implement features of some embodiments of the disclosed technology. The computing system 1000 may be used to implement any of the entities, components or services depicted in the examples of FIGS. 1-9 (and any other components described in this specification). The computing system 1000 may include one or more central processing units ("processors") 1005, memory 1010, input/output devices 1025 (e.g., keyboard and pointing devices, display devices), storage devices 1020 (e.g., disk drives), and network adapters 1030 (e.g., network interfaces) that are connected to an interconnect 1015. The interconnect 1015 is illustrated as an abstraction that represents any one or more separate physical buses, point to point connections, or both connected by appropriate bridges, adapters, or controllers. The interconnect 1015, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 1010 and storage devices 1020 are computer-readable storage media that may store instructions that implement at least portions of the described technology. In addition, the data structures and message structures may be stored or transmitted via a data transmission medium, such as a signal on a communications link. Various communications links may be used, such as the Internet, a local area network, a wide area network, or a point-to-point dial-up connection. Thus, computer-readable media can include computer-readable storage media (e.g., "non-transitory" media) and computer-readable transmission media.

The instructions stored in memory 1010 can be implemented as software and/or firmware to program the processor(s) 1005 to carry out actions described above. In some embodiments, such software or firmware may be initially provided to the computing system 1000 by downloading it from a remote system through the computing system 1000 (e.g., via network adapter 1030).

The technology introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

We claim:

1. A computer-implemented method, comprising:
   receiving, by a computing system, a health goal for a user enrolled in a campaign program, the campaign program specifying a set of tasks to be performed by the user to achieve the health goal;
   generating, by the computing system and based on the health goal for the user, a plurality of messages having information related to a campaign program, the messages being customized for the user, the plurality of messages stored in a plurality of interaction components generated using an interaction component creation tool executing at a computer, wherein each of the interaction components includes an entry link and an exit link, the entry link specifying a previous interaction component of the interaction components that precedes the corresponding interaction component in the sequence, the exit link specifying a next interaction component of the interaction components which follows the corresponding interaction component in the sequence; and
   sending, by the computing system, the messages to a mobile computing device of the user in a sequence, at least one of the messages eliciting the user to respond, wherein a next message of the sequence sent to the user is based on a response received from the user for a previous message of the sequence, wherein the sending includes:
   determining, by the computing system, a first interaction component corresponding to the previous message, wherein the first interaction component includes a plurality of exit links, each of the exit links linked to one of the interaction components,
   determining, by the computing system, a first exit link of the exit links that corresponds to the response received from the user,
   retrieving, by the computing system, the next message from a second interaction component of the interaction components to which the first exit link is linked,
   determining, by the computing system, whether the second interaction component includes a first schedule for sending the next message,
   in an event that the second interaction component includes the first schedule, setting, by the computing system, the first schedule as a schedule for sending the next message,
   in an event that the second interaction component does not include the first schedule, determining, by the computing system, a second schedule as the schedule for sending the next message, and
   sending, by the computing system, the next message to the mobile computing device based on the schedule for sending the next message.

2. The computer-implemented method of claim 1, wherein said sending the messages is done by using a messaging service provided by a wireless telecommunications network of the mobile computing device of the user.

3. The computer-implemented method of claim 2, wherein the messaging service provided by the wireless telecommunications network of the mobile computing device of the user is a short messaging service, and wherein the messages are text messages.

4. The computer-implemented method of claim 1, wherein receiving the health goal includes:
   exchanging, by the computing system, a set of messages with the user for receiving the health goal, the set of messages exchanged with the user via at least one of a messaging service provided by a wireless telecommunications network of the mobile computing device of the user or a social networking application executing at the mobile computing device.

5. The computer-implemented method of claim 4, wherein exchanging the set of messages with the user for receiving a health goal for the user includes:
   sending, by the computer system, a first message of the set to a plurality of users requesting the users to enroll for the campaign program; and
   receiving, by the computer system, a plurality of responses from corresponding users via a first set of messages, the first set of messages indicating an enrollment or a non-enrollment of the subset of users for the campaign program.

6. The computer-implemented method of claim 4, wherein exchanging the set of messages with the user for receiving a health goal for the user includes:
   sending, by the computer system, for selection by the user, a plurality of health goals; and
   receiving, by the computer system, a user selection of one of the health goals as the health goal.

7. The computer-implemented method of claim 1, wherein the messages are sent to the user on a user-defined schedule.

8. The computer-implemented method of claim 1 further comprising:
   analyzing the campaign program, including responses received from the user, to generate a first data, the first data including at least one of a response rate, a response speed, a response speed in a given duration, or a drop-off rate.

9. The computer-implemented method of claim 8 further comprising:
   generating, by the computer system, a report having the first data; and
   sending, by the computer system, the report to a campaign manager of the campaign program.

10. The computer-implemented method of claim 1, wherein sending the messages in a sequence includes identifying the sequence using a decision tree that links the messages of the campaign program defining the sequence for the user.

11. The computer-implemented method of claim 1, wherein sending the messages in the sequence includes determining the sequence based on at least one of profile data of the user, demographic data of a plurality of users participating in the campaign program, or clinical data of the plurality of users participating in the campaign program.

12. A computer-implemented method, comprising:
    exchanging, by a server, a first set of text messages with a user for receiving a goal to be achieved by the user in a campaign program, the campaign program including a set of tasks to be performed by the user to achieve the goal, the first set of text messages exchanged between the server and a computing device associated with the user via a wireless telecommunications network of the computing device;

generating, by the server and based on the goal of the user, a second set of text messages having information related to the campaign program, the second set of text messages presenting to the user at least one of information related to the campaign program or a question requesting a response from the user, the second set of text messages stored in a plurality of interaction components generated using an interaction component creation tool executing at a computer, wherein each of the interaction components includes an entry link and an exit link, the entry link specifying a previous interaction component of the interaction components that precedes the corresponding interaction component in the sequence, the exit link specifying a next interaction component of the interaction components which follows the corresponding interaction component in the sequence;

sending, by the server, a first text message of the second set of text messages to the user;

receiving a response from the user for the first text message; and sending, by the server, a second text message of the second set of text messages forming a sequence of text messages, wherein a next text message of the sequence sent to the user is based on a response received from the user for a previous text message of the sequence, wherein the sending includes:
- determining, by the computing system, a first interaction component corresponding to the first text message, wherein the first interaction component includes a plurality of exit links, each of the exit links linked to one of the interaction components,
- determining, by the computing system, a first exit link of the exit links that corresponds to the response received from the user,
- retrieving the second text message from a second interaction component of the interaction components to which the first exit link is linked,
- determining whether the second interaction component includes a first schedule for sending the second text message,
- in an event that the second interaction component includes the first schedule, setting the first schedule as a schedule for sending the second text message,
- in an event that the second interaction component does not include the first schedule, determining a second schedule as the schedule for sending the second text message, and
- sending the second text message to the user based on the schedule for sending the next message.

13. The computer-implemented method of claim 12, wherein exchanging a first set of text messages includes:
exchanging the first set of text messages with a plurality of users, and
receiving a plurality of goals of the corresponding users.

14. The computer-implemented method of claim 13, wherein generating a second set of text messages includes generating the second set of text messages for each of the users and based on the goals of the corresponding users.

15. The computer-implemented method of claim 12, wherein the goal is a health goal or a behavior change goal of the user.

16. A computer-implemented method, comprising:
outputting, to a campaign manager at a machine-implemented processing system, a graphical user interface (GUI) for generating a campaign program, the GUI including an interaction component creation tool to generate a plurality of interaction components of a plurality of types, the interaction components configured to store a plurality of messages that present to a plurality of users at least one of information related to the campaign program or questions requesting a response from the users;

generating, by the campaign manager and using the interaction component creation tool, the interaction components, each of the interaction components having a specific message that presents at least one of a specific information item regarding the campaign program or a specific question requesting a response from the users, wherein each of the interaction components includes an entry link and an exit link, the entry link specifying a previous interaction component of the interaction components that precedes the corresponding interaction component in the sequence, the exit link specifying a next interaction component of the interaction components which follows the corresponding interaction component in the sequence; and linking, by the campaign manager, the interaction components to form a decision tree, the decision tree identifying a sequence in which the messages of the corresponding interaction components are to be sent to the users, the decision tree identifying, for each of the users, a particular message of the messages to be sent to the corresponding user for a particular response from the corresponding user, wherein the linking includes:
- determining, by the computing system, a first interaction component corresponding to a first message sent to the corresponding user, wherein the first interaction component includes a plurality of exit links, each of the exit links linked to one of the interaction components,
- determining, by the computing system, a first exit link of the exit links that corresponds to the particular response received from the corresponding user,
- retrieving the particular message from a second interaction component of the interaction components to which the first exit link is linked,
- determining, by the computing system, whether the second interaction component includes a first schedule for sending the next message,
- in an event that the second interaction component includes the first schedule, setting, by the computing system, the first schedule as a schedule for sending the particular message,
- in an event that the second interaction component does not include the first schedule, determining, by the computing system, a second schedule as the schedule for sending the particular message, and
- identifying the particular message to be sent to the corresponding user based on the schedule for sending the next message.

17. The computer-implemented method of claim 16, wherein each of the messages is presented to the users as a text message on a mobile computing device associated with corresponding user.

18. The computer-implemented method of claim 17, wherein the text message is a character string, the character string having a specified maximum length.

19. The computer-implemented method of claim 17, wherein the text message is of a plurality of languages.

20. The computer-implemented method of claim 16, wherein the types of the interaction component includes a first type of the interaction component that does not require a response from a user of the users and a second type of the interaction component that requires a response from the user.

21. The computer-implemented method of claim 20, wherein the response for the second type of the interaction component specifies a user selection of a plurality of choices presented to the user in a message of an interaction component of the second type.

22. The computer-implemented method of claim 21, wherein the interaction component of the second type has a plurality of exit links, and wherein linking the interaction component includes:
    linking, for each of the choices, a corresponding exit link to a specific interaction component of the interaction components to be sent to the user in response to receiving a reply from the user containing the corresponding choice.

23. The computer-implemented method of claim 16, wherein the types of the interaction component includes an open type of the interaction component that present messages to the users for which the users can either respond or not.

24. The computer-implemented method of claim 16, wherein each of the interaction components includes a scheduling parameter to indicate a schedule for sending the corresponding messages to the corresponding users.

25. An apparatus, comprising:
    a processor;
    a goal setting module invocable by the processor to exchange a first set of messages with a user for receiving a health goal for the user, the first set of messages exchanged between the computing system and a mobile computing device associated with the user;
    a campaign generation module invocable by the processor to generate, based on the health goal for the user, a plurality of messages having information related to a campaign program, the campaign program specifying a set of tasks to be performed by the user to achieve the health goal, the messages being customized for the user, the plurality of messages stored in a plurality of interaction components, wherein each of the interaction components includes an entry link and an exit link, the entry link specifying a previous interaction component of the interaction components precedes the corresponding interaction component in the sequence, the exit link specifying a next instance of the instances which follows the corresponding instance in the sequence; and
    a campaign messaging module invocable by the processor to send the messages to the mobile computing device of the user in a sequence, wherein a next message of the sequence sent to the user is based on a response received from the user for a previous message of the sequence, wherein the campaign messaging module is configured to send the messages by:
        determining, by the computing system, a first interaction component corresponding to the previous message, wherein the first interaction component includes a plurality of exit links, each of the exit links linked to one of the interaction components,
        determining, by the computing system, a first exit link of the exit links that corresponds to the response received from the user,
        retrieving the next message from a second interaction component of the interaction components to which the first exit link is linked,
        determining, by the computing system, whether the second interaction component includes a first schedule for sending the next message,
        in an event that the second interaction component includes the first schedule, setting, by the computing system, the first schedule as a schedule for sending the next message,
        in an event that the second interaction component does not include the first schedule, determining, by the computing system, a second schedule as the schedule for sending the next message, and
        sending the next message to the mobile computing device based on the schedule for sending the next message.

26. The apparatus of claim 25 further comprising:
an analytics module invocable by the processor to analyze the campaign program, including responses received from the user, to generate a first data, the first data including at least one of a response rate, a response speed, a response speed in a given duration, or a drop-off rate.

27. The apparatus of claim 25 further comprising:
a graphical user interface (GUI) presentation module invocable by the processor to output, to a campaign manager, a GUI for generating the campaign program, the GUI including the plurality of interaction components, the plurality of interaction components being of a plurality of types.

28. The apparatus of claim 27 further comprising:
an interaction component generation module invocable by the processor to generate the interaction components, each of the interaction components having a specific message that presents at least one of a specific information item regarding the campaign program or a specific question requesting a response from a plurality of users; and
a decision tree creation module invocable by the processor to link the interaction components to form a decision tree, the decision tree identifying a sequence in which the messages of the corresponding interaction components are to be sent to the users, the decision tree identifying, for each of the users, a particular message of the messages to be sent to the corresponding user for a particular response from the corresponding user.

* * * * *